United States Patent [19]

James

[11] 4,432,359

[45] Feb. 21, 1984

[54] EQUIPMENT FOR HANDLING INVALIDS AND THE DISABLED

[75] Inventor: David R. James, Glenyard, England

[73] Assignee: James Industries Limited, Gloucester, England

[21] Appl. No.: 377,358

[22] Filed: May 12, 1982

[30] Foreign Application Priority Data

May 16, 1981 [GB] United Kingdom ................. 8115068

[51] Int. Cl.³ ............................................ A61F 13/00

[52] U.S. Cl. .................................... 128/134; 5/81 R; 297/487

[58] Field of Search .................... 128/134, 133, 70–74, 128/80 G; 297/464, 487; 5/81 R

[56] References Cited

U.S. PATENT DOCUMENTS

| | | | |
|---|---|---|---|
| 3,453,026 | 7/1969 | Paes et al. | 297/487 |
| 4,193,147 | 3/1980 | Fischer | 5/81 R |
| 4,300,788 | 11/1981 | Sperling | 297/487 |

FOREIGN PATENT DOCUMENTS

| | | | |
|---|---|---|---|
| 92208 | 9/1959 | Netherlands | 297/487 |

*Primary Examiner*—John D. Yasko

*Attorney, Agent, or Firm*—Allison C. Collard; Thomas M. Galgano

[57] ABSTRACT

Equipment for transporting and lifting invalids and disabled persons comprises a wheeled chassis 1,a telescopic lifting column 2 and a patient support structure 4 supported by an arm 3 from the column 2. The structure 4 is of adjustable articulated form and comprises a central seat section 20 and adjustable end sections 21 22, adjustment of which allows a patient to be supported either in a lying down position or in a seated position facing one way or the other. Restraining means for use with a seated patient comprise an L-shaped member 27 with a first portion 28 which in operative position extends above the seat portion 20 in front of the patient and an end restraining portion 29 which then extends alongside the body of the patient. The member 27 can be turned in a mounting boss 30 to position the portion 29 according to the seated direction used, and the boss 30 turns on a spindle 17 to allow the member 27 to be raised to an inoperative position at the side of the support structure 4.

12 Claims, 11 Drawing Figures

EQUIPMENT FOR HANDLING INVALIDS AND THE DISABLED

BACKGROUND OF THE INVENTION

1. Field of the Invention

This invention relates to equipment for handling invalids and the disabled. It is particularly concerned with equipment for transporting and/or lifting invalids and disabled persons generally, hereinafter referred to generically as "patients", which employs patient support means comprising an articulated structure which is adjustable so that a patient can be supported either in a lying-down position or in a seated position.

2. Description of the Prior Art

Such equipment is commonly used, for example, for transporting patients between a hospital ward and a bathroom, with the support means mounted on a lifting column itself supported on a wheeled chassis. When the patient is transported in a seated position it is usually desirable, if not essential, that some means of restraint be provided to ensure that the patient does not fall off, and various strap and guard rail arrangements have been employed for this purpose. The most acceptable arrangement at present in use comprises a guard rail structure attached to the side of the support structure, but this has the disadvantage that it must be removed during loading and unloading of the patient, and that even if removal is not essential before the supported patient can be lowered into a bath it normally has to be removed during bathing to allow satisfactory access to the patient. The necessity for frequent attachment and detachment of the guard rail is a considerable disadvantage, and it is a nuisance to the nursing staff who are tempted to discard it entirely so that the patient is placed at risk during transport.

SUMMARY OF THE INVENTION

The object of the invention is to provide restraining means which do not suffer from the disadvantages of existing arrangements, particularly in not requiring frequent removal and refitting, and which are generally more convenient to use than existing arrangements. Thus the means of the invention can materially contribute to both nursing morale and patient safety.

According to the invention equipment for handling invalids and disabled persons comprises an articulated patient support structure adjustable for supporting the patient either lying down or seated so as to face, alternatively, in either direction longitudinally of the support structure, and restraining means with a first portion to extend laterally above a central seat section of the support structure and a sideways extending retaining portion to extend alongside the body of a seated patient with said first portion extending in front of the body and above the legs of the patient. The arrangement is such that when the restraining means are in an operative position the restraining portion thereof can be rotated through an angle (preferably an angle of about or slightly more than 180°) so that it alternatively extends to one side or the other according to the direction in which the seated patient faces, with the restraining means furthermore being mounted so as to be pivotable upwardly as a whole from that operative position to an inoperative position at one side of the support structure so that loading and unloading, and bathing, of the patient is not obstructed.

The restraining portion may be rotatably mounted, so that it can be turned through said angle, on the end of said first portion of the restraining means. However, it is preferred that the two portions should comprise a single member which turns as a whole with respect to a pivotal mounting and in this case that member is conveniently generally L shaped and of tubular metal construction. Said pivotal mounting may be a boss with a pivot bore in which the L-shaped member can be rotated through said angle and a second pivot bore which allows the boss to turn on a fixed mounting spindle to provide the pivotal movement of the restraining means between said operative and inoperative positions.

The restraining means are preferably mounted on a drop arm or bracket, or the like, on which the support structure is supported through a cantilever lifting arm from a support column of the equipment. In a preferred construction this supporting bracket is integral with said central seat section of the support structure. The support structure may be detachable from the lifting arm so that the lifting mechanism of the equipment can be used, when desired, with a patient support structure of different type.

The support structure preferably comprises said central seat section to which are articulated two identical end sections alternatively usable as back-support or leg-support sections according to the patient seating direction to be used. With equipment embodying a wheeled chassis a patient is desirably transported with the chassis wheeled in the longitudinal direction of the supporting structure, i.e. with the seated patient facing in the direction of travel. To facilitate this the outer end corners of the end sections of the support structure may provide hand grips for use by an attendant when pushing the patient.

If the support structure is designed to fit into a bath the end sections cannot be long enough to provide a headrest and thus can merely serve for either back or leg support. In view of this, equipment in accordance with the invention may be provided with an adjustable and removable headrest which can be fitted on to either one of the end sections according to which one thereof is at the time being used as a backrest.

Adjustment means, to adjust the relative angular positions of the seat section and each end section, may comprise a link pivotally attached at one end to the corresponding end section (or the central seat section) and adjustably secured at the other end to the seat section (or the corresponding end section). The adjustment may be achieved by selective detent-like engagement of said other end of the link with a series of notches in a notched member secured at the side of the corresponding section.

Other features of the invention will be apparent from the following description, drawings and claims, the scope of the invention not being limited to the drawings themselves as the drawings are only for the purpose of illustrating a way in which the principles of the invention can be applied. Other embodiments of the invention utilizing the same or equivalent principles may be used and structural changes may be made as desired by those skilled in the art without departing from the present invention and the purview of the appended claims.

DESCRIPTION OF THE PREFERRED EMBODIMENTS

Figure 1:
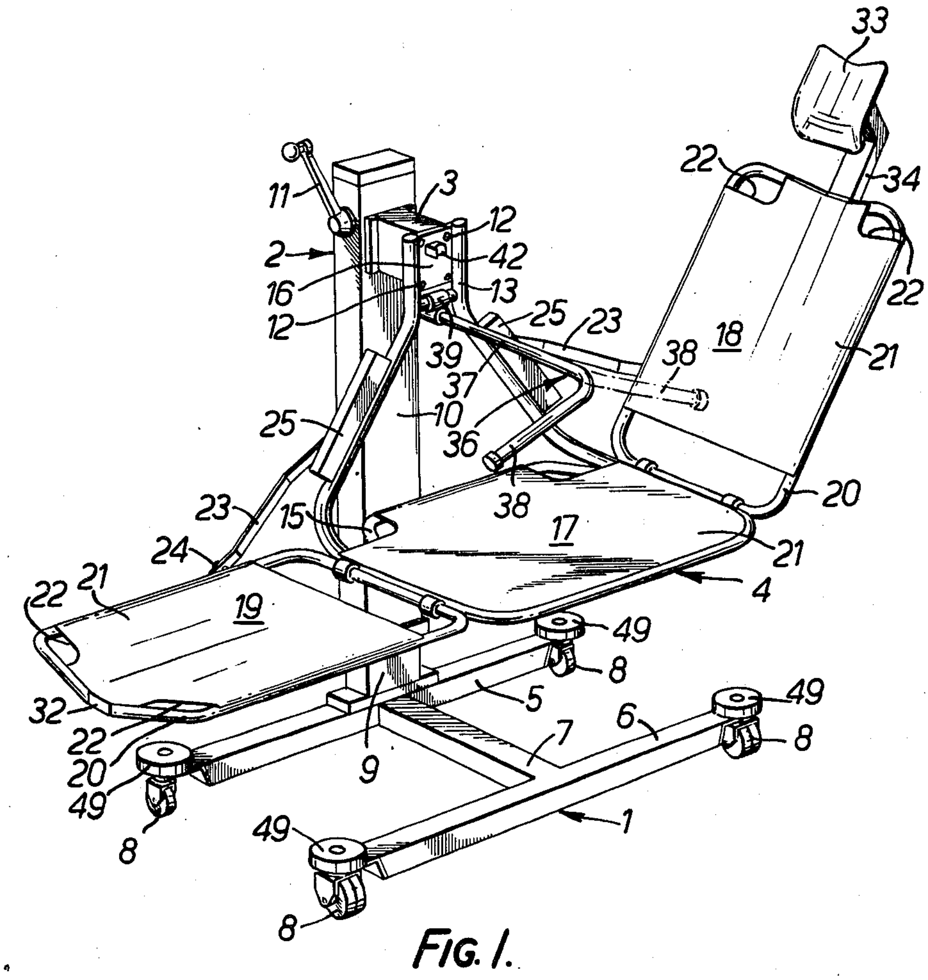
FIG. 1 is a diagrammatic front perspective view of the patient lifting and transporting equipment in accordance with the invention.
Figure 5:
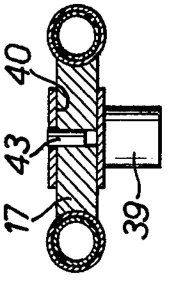
FIG. 5 is a fragmentary sectional view on the line V—V in FIG. 2.

The construction illustrated comprises a wheeled chassis 1, an upstanding telescopic lifting column 2 which is mounted centrally at one side of the chassis 1, a short cantilever lifting arm 3 which projects from the column 2, and a patient support structure 4 supported by the arm 3. The chassis 1 is of "H" form with longitudinal members 5 and 6, on the former of which the column 2 is mounted and which are joined by a central cross member 7. Four castors 8 are respectively mounted at the ends of the longitudinal members 5,6. The lifting column 2 comprises telescopic portions 9 and 10, the lower portion 9 being fixed to the chassis member 5 and the upper portion 10 to which the arm 3 is secured being raised and lowered by means of an internal screw-jack mechanism (not illustrated) operated by a top winding handle 11. Thus the lifting arm 3 is raised and lowered with the upper column portion 10 by turning the handle 11 in the appropriate direction.

The support structure 4 has an integral support bracket 13 detachably secured to the outer end of the short frame 3 and of a tubular metal construction presenting, when viewed laterally of the support structure 4, the appearance of an A-frame. This bracket 13 (see particularly FIGS. 2 and 3) consists of a generally vertical A-frame portion 14 continued as a bottom central frame portion 15 of the support structure 4. The top apex of the "A" is provided by a plate 16 which is flange-bolted to the support frame 3 by four bolts 12, and the intermediate limb of the "A" is a short length of steel rod 17 providing a pivot spindle for said restraining means of the invention.

Said support structure 4 comprises a central seat section 17 including the described frame portion 15 integral with the bracket 13, and identical end sections 18,19 which are freely articulated to the central section 17 at opposite ends of the latter. Each of the end sections 18,19 comprises a tubular metal frame 20, of closed-loop and rectangular plan form, and a covering panel 21 of suitable plastics material, for example, is attached to the frame of each section 17,18 or 19. These panels 21 can be moulded or otherwise shaped or treated to provide the desired surface conformation or finish, such as an anti-slip surface. The panel 21 of the central seat section 17 can, for example, be provided with a moulded recess or recesses engageable by the buttocks of a seated patient to prevent the patient slipping along the seat during transport. The outer corners of the panels 21 of the end sections 18,19 are cut away as at 22 to expose the corners of the end frames 20, which are thus accessible for use as handgrips by an attendant while pushing the equipment during transport of a patient on the support structure 4.

Adjustment means are provided which allow the relative angles of the central seat section 17 and the end sections 18,19 of the support structure 4 to be adjusted independently and retained at the adjusted values. These adjustment means, the component parts of which are shown in detail in FIGS. 9 to 11, comprise in each case a link 23 pivotally mounted at 24 to the frame 20 of the corresponding end section 18 or 19 and at the other end engaging in a detent-like manner with a notched member 25 welded to the adjacent side member of the A-frame 14. It will be appreciated that these components could be reversed, with each link 23 pivotally mounted with respect to the central section 17 and the notched member 25 mounted on the corresponding end section 18 or 19.

Figure 9:
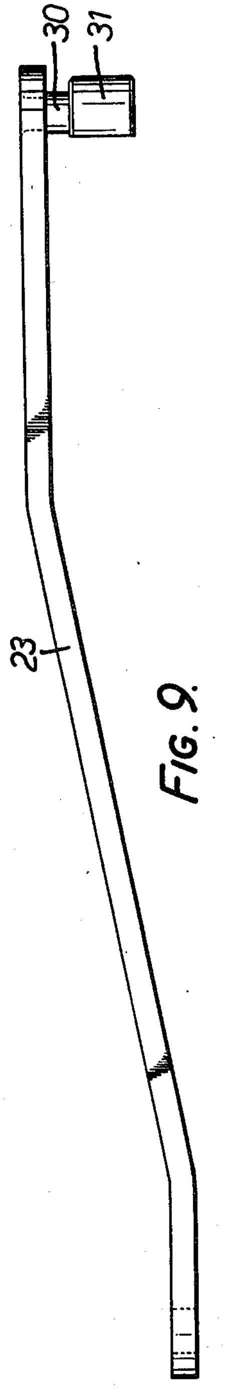
FIGS. 9 and 10 are detail views of components of adjustment means of the frame of FIG. 2.
Figure 10:
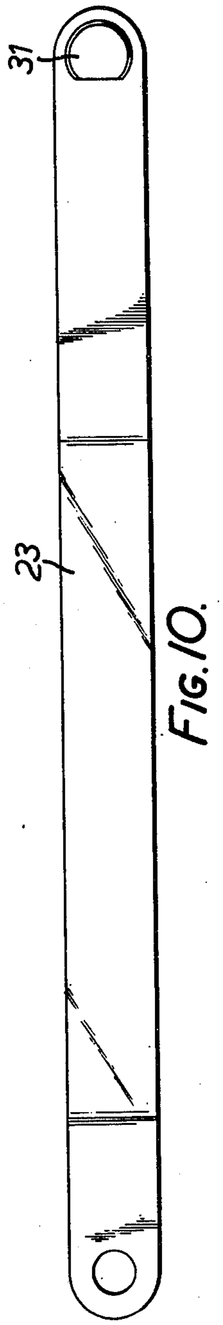
Figure 11:
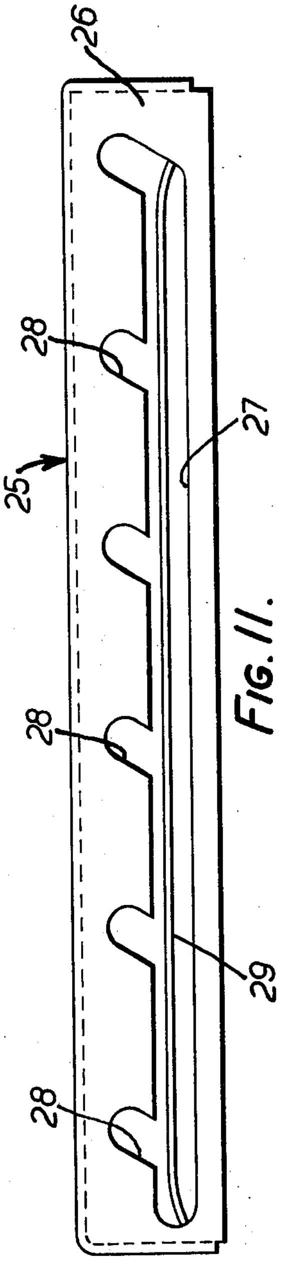

Referring particularly to FIGS. 9 to 11, the notched member 25 is of elongated box-like form with a side wall 26 which has a longitudinal notched slot 27 providing a spaced series of detent notches 28. A leaf spring 29 extends longitudinally within the member 25 and the link 23 has, at the adjacent end, a projecting pin 30 which can be selectively engaged with the notches 28 for the purpose of adjustment. The pin 30 fits the notches and has an enlarged head 31 which retains the pin within the member 25, and this head 31 engages with the spring 29 which thus applies a spring force holding the pin 30 in the selected notch 28. This prevents accidental disengagement as positive effort is required to move the pin 30 against the spring 29 before the pin 30 can be moved to engage a different notch 28. When the pin 30 is engaged with the end notch 28 at the limit of adjustment the corresponding end section 18 or 19 lies flat with the central section 17, as shown with the end section 19 in FIG. 1. With both the end sections 18,19 so adjusted a patient is supported lying flat on the support structure 4. For seated support of a patient either of the end sections 18 or 19 can be adjusted, as shown with the section 18 in FIG. 1, so that this section can act as a back-rest and this adjustment is effected by moving the pin 30 of the corresponding adjustment means to an appropriate notch 28 in the element 25.

Figure 2:
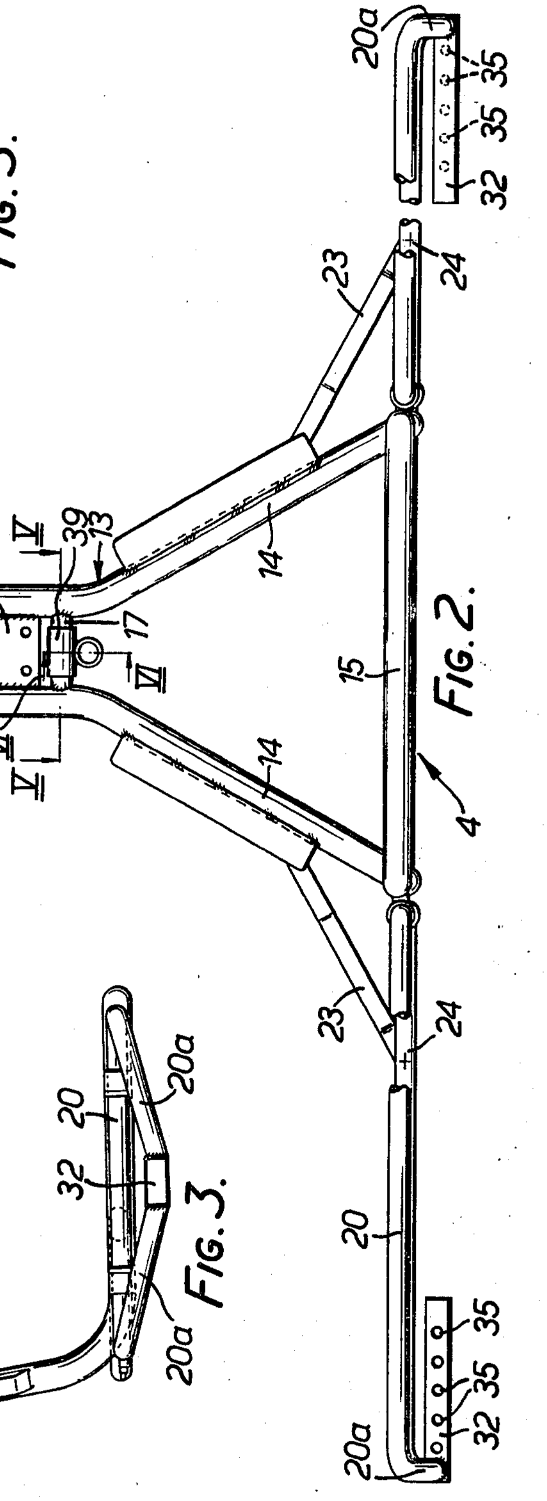
FIG. 2 is a front detail view of an integral support bracket/seat section frame of the equipment illustrated.
Figure 3:
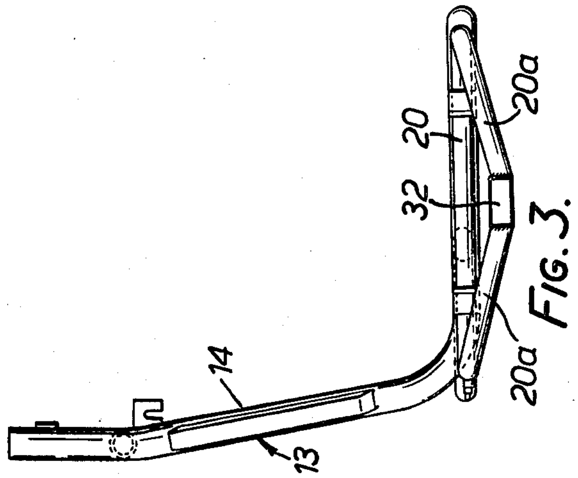
FIGS. 3 and 4 are corresponding side and top views.
Figure 4:
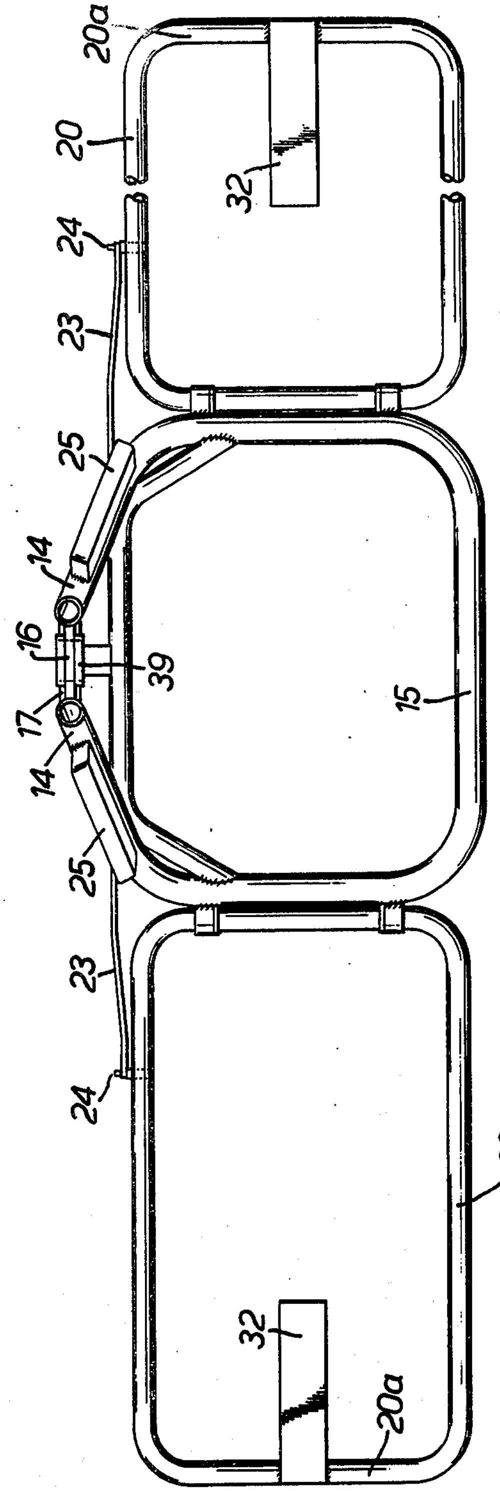

As shown more particularly in FIGS. 2 and 3, each of the end frames 20 has an end limb *20a* which is bent out of the general plane of the frame 20, and a rectangular-section socket 32 is welded into the center of this limb *20a*. This allows a removable moulded head-rest 33 to be attached to either of the end sections 18 or 19 when that section is used as a back-rest with a seated patient, as illustrated with the section 18 in FIG. 1. The head-rest 33 is of adjustable height, and to this end it has a rectangular section stem 34 which fits telescopically into either of the sockets 32. The height adjustment is retained by a spring loaded detent pin (not shown) in the stem 34 which can selectively be engaged with any one of a row of detent bores such as 35 in one side wall of the socket 32.

Said restraining means comprise a tubular L-shaped member 36, with a first mounting portion 37 which extends horizontally (when in operative position as shown in FIG. 1) above the seat section 17 and a laterally extending restraining portion 38. The portion 37 is pivotally mounted in a pivot boss 39 (see particularly FIGS. 6 to 8) with offset pivot bores 40 and 41 disposed at right angles to each other. The bore 40 mounts the restraining means on said spindle 17 of the A-frame 14 while the restraining member 36 is mounted in the bore 31.

In the operative position of the boss 39 shown in FIG. 1, the member 36 can be turned in the bore 41 through an angle of slightly more than 180° centered about the vertical so that the portion 38 extends either to the left and slightly downwardly (as shown in full lines) or to the right and slightly downwardly (as shown in broken lines). In the former case it is designed to restrain a seated patient while using the end support section 19 as a back-rest, whilst in the latter case it is operative to restrain a seated patient while using the end section 19 as a back-rest. For loading and unloding the patient, or during bathing for example, the restraining means can be pivoted upwardly and out of the way to an inoperative stowed position (not shown), in which the mounting portion 37 extends upwardly and clips into a spring clip 42 secured to the plate 16. During movement between the operative and inoperative positions of the restraining means, the boss 39 turns on the spindle 17.

Figure 6:
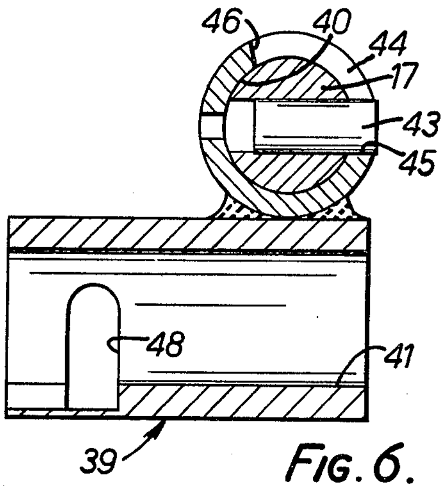
FIG. 6 is a sectional view on the line VI—VI in FIG. 2.
Figure 7:
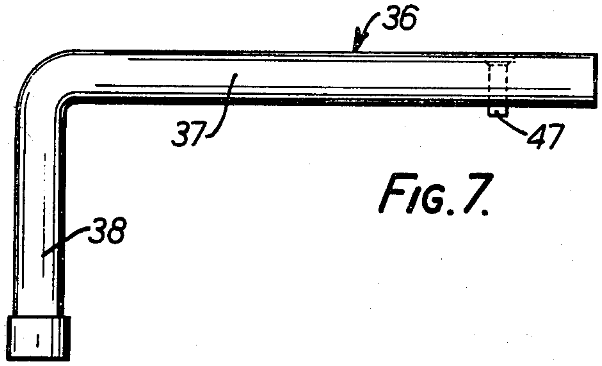
FIG. 7 is a detail view of a restraining element of the equipment.
Figure 8:
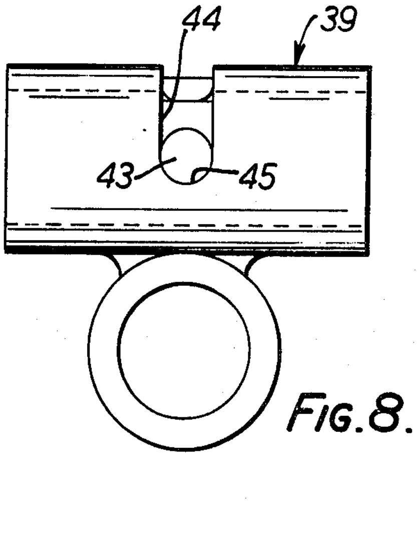
FIG. 8 is a detail view of a pivotal mounting boss of the restraining element, also shown in section in FIG. 6.

Lateral location of the boss 39 on the spindle 17 is provided by a cross pin 43 which projects radially at one side from the spindle 17 into a through slot 44 in the wall of the bore 40. The ends 45 and 46 of the slot 44 limit movement of the boss 39 on the spindle 17—engagement of the pin 43 with the end wall 45 as shown in FIGS. 6 and 8 defines the lowered operative position of the boss 39 and restraining means, and engagement with the other end 46 defines the raised inoperative position of the restraining means. A cross pin 47, which similarly projects adjacent the mounted end of the portion 37 of the restraining member 36, moves in a through slot 48 in the wall of the bore 41. The ends of the slot 48 similarly limit turning of the restraining member 36 in the bore 47 to define, respectively, the left-hand and right-hand restraining positions of the restraining portion 38.

Freely rotatable circular discs 49, respectively mounted on each of the ends of the chassis members 5,6 about vertical rotational axes, are rubber tired and serve to prevent or minimise damage to the walls or furniture with which the chassis may inadvertently collide during transport of the patient.

In a modified construction, which is not illustrated, the restraining member 36 is non-rotatably fixed in the pivot boss 39 and the member is formed as two spearate portions with the restraining portion 38 rotatably mounted on the end of the mounting portion 37. This allows the required movement of the portion 38 between its left-hand and right-hand operative positions.

While I have illustrated and described my invention in its preferred form, it will be apparent that the same is subject to alteration and modification without departing from the underlying principles involved, and we accordingly do not desire to be limited to the specific details illustrated and described except as may be necessitated by the appendant claims.

I claim:

1. Equipment for handling invalids and disabled persons, comprising an articulated patient support structure with a central section and end sections separately adjustable relative to the central section for supporting the patient either lying down or seated so as to face, alternatively, in either direction longitudinally of the support structure, and restraining means with a first portion to extend laterally above said central section of the support structure with a patient seated thereon and a sideways extending retaining portion to extend alongside the body of the seated patient with said first portion of the restraining means extending in front of the body and above the legs of the patient, said restraining means being such that when in an operative position the restraining portion thereof is rotatably through an angle such that it can alternatively extend to one side or the other according to the direction in which the seated patient faces and said restraining means being so mounted as to be rotatable upwardly as a whole from said operative position to a raised inoperative position at one side of the support structure.

2. Equipment according to claim 1, wherein said angle through which said restraining portion can be rotated, when the restraining means are in said operative position, is an angle of slightly more than 180°.

3. Equipment according to claim 1, wherein said restraining portion is rotatably mounted on the end of said first portion of the restraining means.

4. Equipment according to claim 1, wherein said two portions of said restraining means comprise a single member which turns as a whole with respect to a pivotal mounting thereof.

5. Equipment according to claim 4, wherein said single member is generally L-shaped of tubular metal construction.

6. Equipment according to claim 4, wherein said pivotal mounting is a boss with a first pivot bore in which said single member can be rotated through said angle and with a second pivot bore by which the boss itself is mounted on a fixed mounting spindle and which allows the boss to turn thereon to provide pivotal movement of the restraining means between said operative and inoperative positions.

7. Equipment according to claim 1, wherein the equipment includes a column from which the patient support structure is supported through a drop arm or bracket, or the like, and a lifting mechanism whereby the drop arm or bracket can be raised and lowered, and wherein the restraining means is mounted on said drop arm or bracket.

8. Equipment according to claim 7, wherein said column is mounted on a wheeled chassis and is positioned at one side thereof with the patient support structure extending above the chassis.

9. Equipment according to claim 7, wherein at least a portion of the drop arm or bracket on which the restraining means is mounted is integrated with said central seat section of the support structure.

10. Equipment according to claim 7, wherein the support structure is detachable from said column so that ,15 the lifting mechanism of the equipment can when desired be used with a patient support structure of different type.

11. Equipment according to claim 1, including an adjustable head rest which can be fitted on to either one of said end sections of the support structure, according to which one thereof is at the time being used as a back rest.

12. Equipment according to claim 1, wherein adjustment means are provided which allow the relative angles of said central seat section and said end sections of the support structure to be adjusted and retained at the adjusted values, said adjustment means comprising for each end section a link pivotally connected at one end to the corresponding end section (or the central section) and the other end of which selectively engages in a detent-like manner with a series of notches formed in a notched member mounted on and extending alongside the central section (or the corresponding end section), spring-loading means providing a spring force against which the link has to be displaced for disengagement from a notch for adjustment of the corresponding end section, while in use of the equipment the spring force acts to retain the link in the selected notch.

* * * * *